(12) United States Patent (10) Patent No.: US 7,816,096 B2
Fang et al. (45) Date of Patent: Oct. 19, 2010

(54) ASSAY SOLUTION COMPOSITIONS AND METHODS FOR GPCR ARRAYS

(75) Inventors: Ye Fang, Painted Post, NY (US); Ann M. Ferrie, Painted Post, NY (US); Yulong Hong, Painted Post, NY (US); Sadashiva K. Pai, Painted Post, NY (US); Jinlin Peng, Painted Post, NY (US); Brian L. Webb, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 12/697,664

(22) Filed: Feb. 1, 2010

(65) Prior Publication Data

US 2010/0152060 A1 Jun. 17, 2010

Related U.S. Application Data

(63) Continuation of application No. 11/312,776, filed on Dec. 21, 2005, now Pat. No. 7,682,802, which is a continuation of application No. 10/676,351, filed on Sep. 30, 2003, now abandoned.

(51) Int. Cl.
 *G01N 33/53* (2006.01)
 *G01N 33/543* (2006.01)

(52) U.S. Cl. .................. 435/7.21; 435/7.1; 436/501; 436/518; 424/9.1; 424/164.1; 530/300; 530/350; 530/356

(58) Field of Classification Search ................ None
 See application file for complete search history.

(56) References Cited

OTHER PUBLICATIONS

J. Drews, "Drug Discovery: A Historical Perspective", Mar. 17, 2000, vol. 287, Science, pp. 1960-1964.
P. Ma et al., "Value of Novelty?", Nature Reviews, Drug Discovery, vol. 1, Aug. 2002, pp. 571-572.
K.L. Pierce et al., "Seven-Transmembrane Receptors", Nature Reviews, Molecular Cell Biology, vol. 3, Sep. 2002, pp. 639-650.
A.D. Howard et al., "Orphan G-protein-coupled receptors and natural ligand discovery", TRENDS in Pharmacological Sciences, vol. 22, No. 3, Mar. 2001, pp. 132-140.
I.A. Hemmilä et al., "Novel detection strategies for drug discovery", DDT, vol. 7, No. 18 (Suppl.), 2002, pp. S150-S156.
J.C. Ventor et al., "The Sequence of the Human Genome", Science, vol. 291, Feb. 16, 2001, pp. 1304-1351.
A.L. Hopkins et al., "The druggable genome", Nature Reviews, Drug Discovery, vol. 1, Sep. 2002, pp. 727-730.
S.L. Schreiber, "Target-Oriented and Diversity-Oriented Organic Synthesis in Drug Discovery", Science, vol. 287, Mar. 17, 2000, pp. 1964-1969.
J. Ziauddin et al., "Microarrays of cells expressing defined cDNAs", Nature, vol. 411, May 3, 2001, pp. 107-110.

O.E. Beske et al., "High-throughput cell analysis using multiplexed array technologies", DDT, vol. 7, No. 18 (Suppl.), 2002, pp. S131-S135.
P. Mitchell, "A perspective on protein microairays", Nature Biotechnology, vol. 20, Mar. 2002, pp. 225-229.
G. MacBcath et al., "Printing Proteins as Microarrays for High-Throughput Function Determination", Science, vol. 289, Sep. 8, 2000, pp. 1760-1763.
Y. Fang et al., "Membrane Protein Microanays", J. Am. Chem. Soc., vol. 124, No. 11, 2002, pp. 2394-2395.
Y. Fang et al., "G protein-coupled receptor microanays for drug discovery", DDT, vol. 8, No. 16, Aug. 2003, pp. 755-761.
Y. Fang et al., "G-protein-coupled Receptor Microarrays", ChemBioChem, 2002, vol. 3, pp. 987-991.
S.R. George et al., "G-Protein-Coupled Receptor Oligomerization and Its Potential for Drug Discovery", Nature, vol. 1, Oct. 2002, pp. 808-820.
S.N. Bailey et al., "Applications of transfected cell microanays in high-throughput drug discovery", DDT, vol. 7, No. 18 (Suppl.), 2002, S113-S135.
H.Y. Erbil et al., "Transformation of a Simple Plastic into a Superhydrophobic Surface", Science, vol. 299, Feb. 28, 2003, pp. 1377-.
B. Schweitzer et al., "Multiplexed protein profiling on microanays by rolling-circle amplification", Nature Biotechnology, vol. 20, Apr. 2002, pp. 359-365.
B. Schweitzer et al., "Immunoassays with rolling circle DNA amplification: A versatile platform for ultrascnsitive antigen detection", Proc. Natl. Acad. Sci., Aug. 29, 2000, vol. 97, No. 18, pp. 10113-10119.
M. Schena et al., "Quantitative Monitoring of Gene Expression Patterns with a Complementary DNA Microarray", Science, vol. 270, Issue 5235, Oct. 20, 1995, pp. 467-470.
Hawes BE and van Biesen T, Current Protocols in Pharmacology, "Protein Tyrosine Kinase Activity Assays", Unit 3.5, pp. 3.5.1 to 3.5.18.
Boehringer Mannheim Corp., 1998 Biochenicals Catalog, pp. 486-493 (1998).

*Primary Examiner*—Lisa V Cook
(74) *Attorney, Agent, or Firm*—John L. Haack

(57) ABSTRACT

Buffered assay solutions for performing 1) binding or 2) functional assays on GPCR arrays, along with methods for their use are described. The buffered assay solution has an underlying composition having: a buffer reagent with a pH in the range of about 6.5 to about 7.9; an inorganic salt of either a monovalent or divalent species, at a concentration from about 1 mM to about 500 mM; and optionally a combination of: c) a blocker reagent at a concentration of about 0.01 wt. % to about 2 wt. % of the composition, or d) protease-inhibitor at a concentration of about 0.001 mM to about 100 mM. In an embodiment for functional assay uses, the composition is modified to also include a GTP-analogue, a guanosine 5'-diphosphate (GDP) salt, and/or an anti-oxidant reagent.

3 Claims, 6 Drawing Sheets

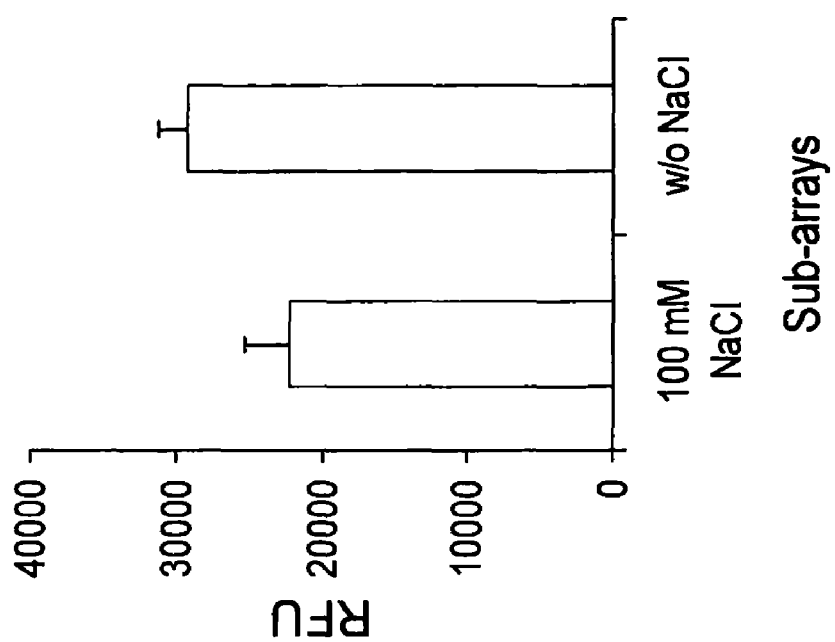

Cocktail labeled ligands
+ 1 µM telenzepine

Cocktail labeled ligands

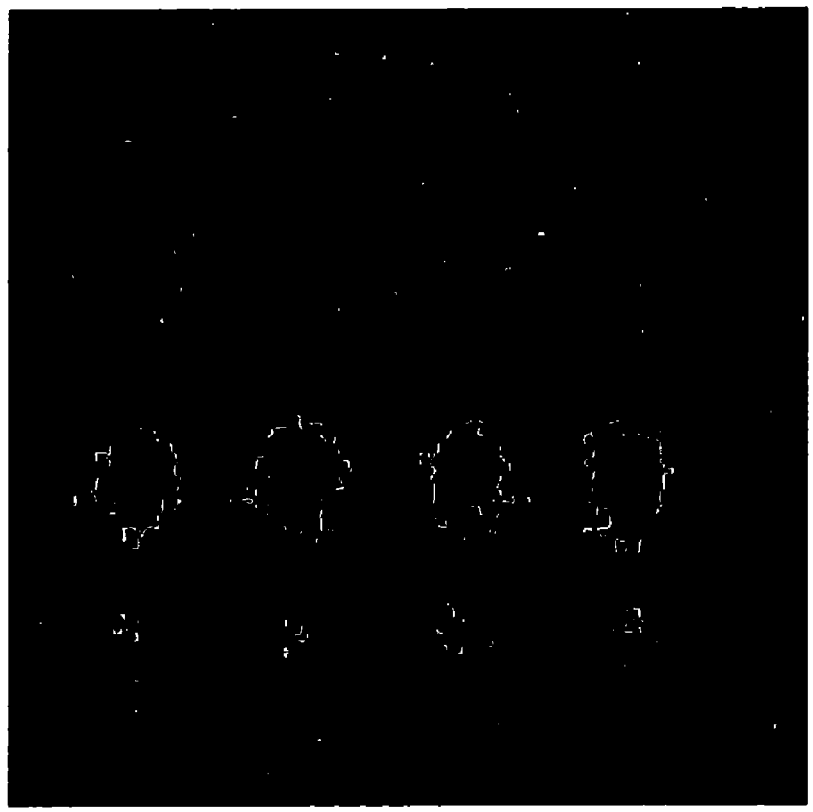
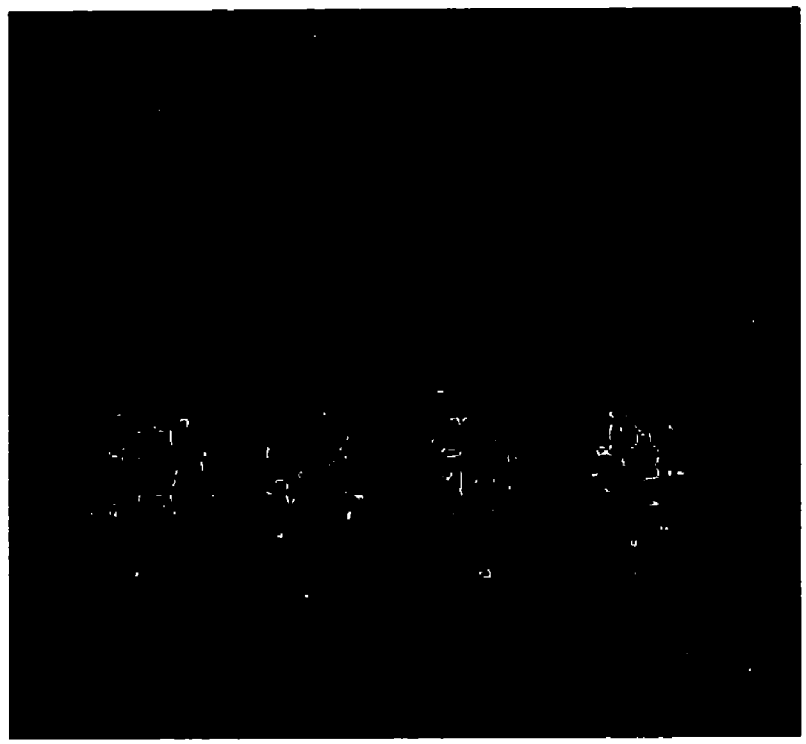

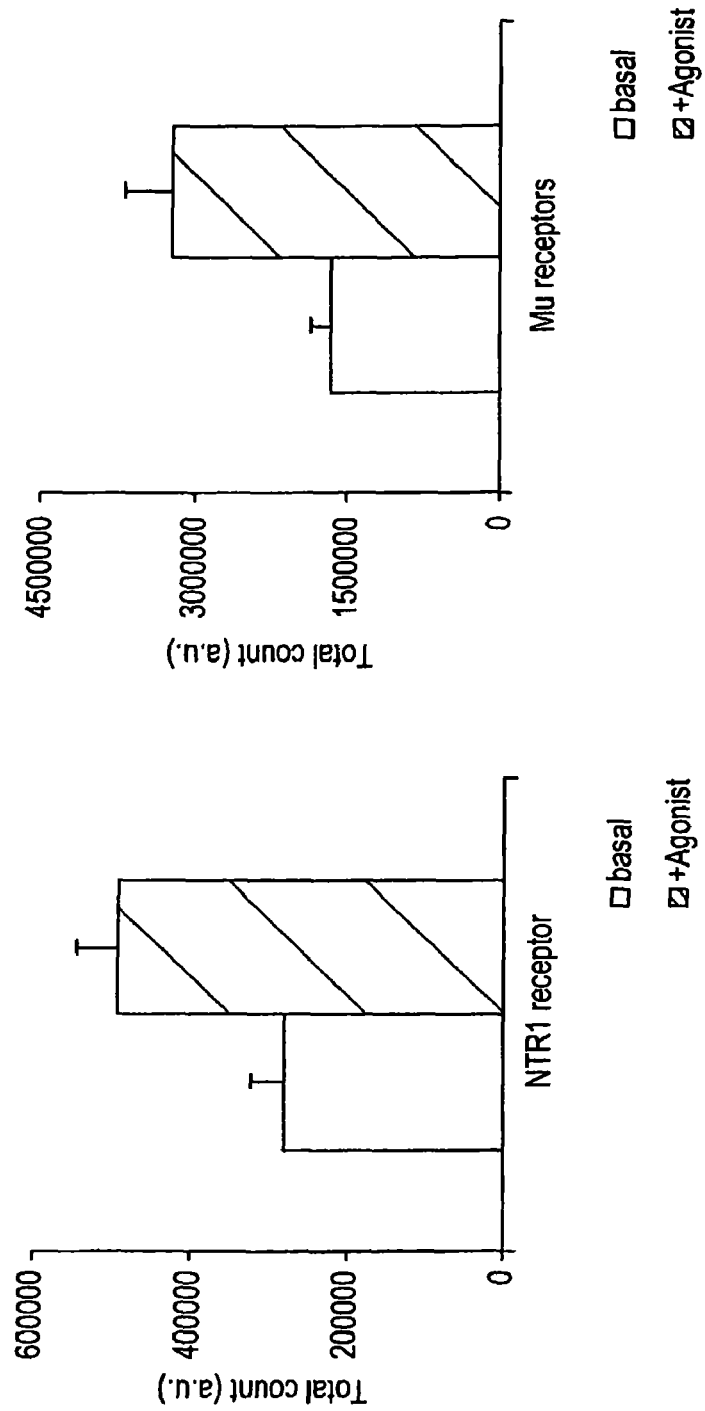

ASSAY SOLUTION COMPOSITIONS AND METHODS FOR GPCR ARRAYS

CROSS-REFERENCE TO RELATED APPLICATIONS

This application is a continuation of and claims the benefit of priority to U.S. patent application Ser. No. 11/312,776, filed Dec. 21, 2005 now U.S. Pat. No. 7,682,802, which is a continuation of U.S. application Ser. No. 10/676,351, filed Sep. 30, 2003 now abandoned, the content of which is incorporated herein by reference in its entirety, and priority benefit under 35 U.S.C. §120 is claimed.

FIELD OF INVENTION

The present invention relates to biological assays. In particular, the invention includes compositions for buffer solutions used with binding and functional assays for GPCR arrays. A method is also included which utilizes negatively-charged polymers and/or water-soluble proteins to reduce the background of such assays and improve signal to background ratios.

BACKGROUND

G-protein-coupled receptors (GPCRs) are one of the most successful target proteins for drug discovery research to date. Approximately 50% of current drugs target GPCRs; about 20% of the top 50 best selling drugs target GPCRs; more than $23.5 billion in pharmaceutical sales annually are ascribed to medications that address this target class. (Drews, J., "Drug Discovery: A Historical Perspective" Science 2000, 287, 1960-1963; Ma, P., and Zemmel, R., "Value of Novelty" Nat. Rev. Drug Discov. 2002, v. 1, 571-572.) Forming a superfamily of seven trans-membrane-spanning proteins that are expressed in virtually all kinds of tissues, GPCRs are associated with almost every major therapeutic category or disease class, including pain, asthma, inflammation, obesity, cancer, as well as cardiovascular, metabolic, gastrointestinal and central nervous system diseases.

The tremendous significance of drugs targeting GPCRs lies in the physiological roles of GPCRs—as cell-surface receptors responsible for transducing exogenous signals into intracellular response(s). (Haga, T., and Berstein, G., eds., G-Protein-Coupled Receptors, CRC Press, Boca Raton, Fla., 1999.) Signaling through these receptors regulates a wide variety of physiological processes, such as neurotransmission, chemotaxis, inflammation, cell proliferation, cardiac and smooth muscle contractility, as well as visual and chemosensory perception. In addition to the role normal receptors play in modulating physiological processes, GPCR mutations that result in both gain and loss of function are associated with certain human diseases. For example, GPCR polymorphisms have been linked with hypertension, idiopathic cardiomyopathy (endothelin A receptor), autosomal dominant hypocalcemia and familial hypocalciuric hypercalcemia (calcium-sensing receptor), follicular maturation arrest and suppression of spermatogenesis (follicle-stimulating hormone receptor), and bronchodilator desensitization and nocturnal asthma (β2-adrenoceptors).

In the human genome there are about 400-700 GPCRs of therapeutic relevance; of these GPCRs, ligands for about 200 have been discovered. (Pierce, K. L. et al., "Seven-Transmembrane Receptors." Nat. Rev. Mol. Cell Biol. 2002, v. 3, 639-650.) Although there is very little conservation at the amino acid level among GPCR sequences, all GPCRs share certain structural and mechanistic features. Typically, GPCRs are formed of seven-helical trans-membrane-spanning domains (each ~20-30 amino acids in length) joined by intra- and extra-cellular loops. The spatial organization of these trans-membrane regions, the extra-cellular N-terminus and the extracellular loops, form the binding sites for extra-cellular ligands. The intracellular loops and carboxyl-terminus form the sites of interaction with signal-transducing heterotrimeric G-proteins and other regulatory proteins, such as receptor kinases and arrestins. A wide variety of ligand species, including biogenic amines, peptides and proteins, lipids, nucleotides, excitatory amino acids and ions, small chemical compounds, etc., can activate GPCRs.

The success of GPCRs as drug targets stems from the fact that the binding of natural ligands to their paired GPCR(s) can be moderated using appropriate small molecule drugs. (Ma, P., and Zemmel, R., "Value of Novelty," Nat. Rev. Drug Discov. 2002, v. 1, 571-572.) Effective engineering of these drugs is, however, critical as aberrant binding to such a physiologically significant target class can lead to serious side effects. Structural data on GPCRs is limited and rational drug design is a significant challenge. Designing drugs that do not bind to non-targeted GPCRs is almost impossible. Currently, selectivity studies are conducted downstream in the drug discovery process—discarding compounds because of adverse binding at this stage makes the drug discovery process both expensive and time consuming. Given these considerations, and the strong possibility that so-called "orphan" GPCRs, recently discovered as a result of the sequencing of the human genome, may be valuable targets (Howard, A. D., et al., "Orphan G-Protein-Coupled Receptors and Natural Ligand Discovery." TiPS 2001, v. 22, 132-140), there is a strong need for technologies that enable screening against multiple GPCRs simultaneously.

Given the importance of G-protein-coupled receptors as drug targets, a wide range of technologies has been developed to screen compounds against GPCRs. (e.g., Hemmila, I. A., and Hurskainen, P., "Novel Detection Strategies for Drug Discovery," Drug Discov. Today 2002, 7, S152-S156.) The increased pace of target identification (Venter, J. C., et al. "The Sequences of the Human Genome," Science 2001, v. 291, 1304-1351; Hopkins, A. L., and Groom, C. R., "The Druggable Genome," Nat. Rev. Drug Discov. 2002, v. 1, 727-730) and the increasing size of compound libraries continues to drive the development of novel GPCR screening technologies (Schreiber, S. L., "Target-Oriented and Diversity-Oriented Organic Synthesis in Drug Discovery," Science 2000, v. 287, 1964-1968). These assays can be classified into cell based and GPCR-membrane based assays. Despite the interest and the overwhelming number of current and future GPCR targets, few methods have been described for simultaneously studying multiple GPCRs. Recently, two groups of researchers have suggested that arrays of transiently transfected cell clusters or GPCR transfected cells on barcoded substrates could be used for multiplexed compound screening. (Ziauddin, J., and Sabatini, D. M., "Microarrays of Cells Expressing Defined cDNAs," Nature 2001, v. 411, 107-110; Beske, O. E., and Goldbard, S., "High-throughput Cell Analysis Using Multiplexed Array Technologies," Drug Discov. Today 2002, v. 7, s131-s135.)

The value of parallel analysis afforded by DNA microarrays (e.g., Schena, M., et al. "Quantitative Monitoring of Gene Expression Patterns with a Complementary DNA Microarray," Science 1995, v. 270, 467-470) has inspired the development of protein arrays (e.g., Mitchell, P., "A Perspective on Protein Microarrays," Nat. Biotechnol. 2002, v. 20, 225-229). Beyond the use of protein abundance profiling as an analogue to gene expression profiling, protein arrays offer the possibility of highly parallel investigations of protein-small molecule and protein-protein interactions. (MacBeath, G., and Schreiber, S. L., "Printing Proteins as Microarrays for High-throughput Function Determination," *Science* 2000, v. 289, 1760-1763; Schweitzer, B., et al. "Immunoassays with Rolling Circle DNA Amplification: A Versatile Platform for Ultrasensitive Antigen Detection," *Proc. Natl. Acad. Sci. USA* 2000, v. 97, 10113-10119; Fang, Y., et al. "Membrane Protein Microarrays," *J. Am. Chem. Soc.* 2002, v. 124, 2394-2395; and Fang, Y., et al. "G-Protein-Coupled Receptor Microarrays for Drug Discovery," *Drug Discov. Today,* 2003, v. 18, 755-761.)

Although the importance of combinatorial approaches to drug design has been realized, the biological equivalent of combinatorial chemistry—multi-target screening using protein microarrays—has not. For multi-target screening, GPCR microarrays maximize the potential for effective matching of biological target space to chemical ligand space. Although, protein microarrays are naturally suited for testing compounds against multiple proteins simultaneously, some of the fundamental aspects of multiplexed bioassays using protein chips are yet to be fully demonstrated. One such fundamental aspect is a need to produce assay conditions, which can lead to optimal binding profiles of any given target compounds and/or labeled ligands to the numerous receptors in the arrays. Problems due to non-specific binding of labeled ligands to the receptor microspots and the background surface, non-optimal interaction of target compounds and labeled ligands with the receptors in the arrays under the assay conditions, and the lack of general guidelines for assay buffer design and selection have deterred scientists from testing the feasibility of multiplexed binding assays for compound profiling and screening.

For functional assays using GPCR microarrays, one should also keep in mind other special considerations in order to achieve not only optimal binding profiling of labeled ligands and target compounds to the receptors in the arrays, but also to maximize the assay sensitivity for monitoring the agonist-induced activation of the receptors and sequential the activation of the G proteins coupled with the receptors. Hence, guidance for assay buffer design and methods to reduce the background are needed for realization of full potentials of GPCR microarrays for compound profiling and screening using multiplexed binding assays and functional assays.

SUMMARY OF THE INVENTION

The present invention provides in part formulations in two embodiments of a buffered solution which can be applied to 1) multiplexed binding assays or 2) functional assays. Typically, in a binding assay, a cocktail of labeled ligands is used to test for or determine the relative, specific, or selective potency of a target compound to bind with a receptor probe in a microarray against its pre-selected labeled-ligand(s). Commonly, each labeled ligand in the cocktail binds with its corresponding receptor. In comparison, a functional assay uses a labeled GTP-analogue for examining or determining physiological functionality of a target compound acting on a receptor probe in a microarray. The labeled GTP-analogue is employed as a substitute for the labeled ligands. The functional assay involves monitoring the "down-stream action" of a probe molecule; that is, the activation of G-protein coupled with the receptor. The binding of an agonist to a receptor results in a conformational change in the receptor, which induces activation of the G-protein.

The buffered solution according to a first embodiment is designed to optimize the binding profiles of target compounds and labeled ligands with GPCRs in a microarray, in preferably multiplexed binding assays. Optimization refers to an ability to derive binding profiles that are either physiologically or pharmacologically relevant. The solution has a composition comprising: a) a buffer reagent with a pH in the range of about 6.5 to about 7.9; b) an inorganic salt of either a monovalent or divalent species, at a concentration from about 1 mM to about 500 mM; and optionally a combination of: c) a blocker reagent at a concentration of about 0.01 wt. % to about 2 wt. % of the composition, or d) protease-inhibitor at a concentration of about 0.001 mM to about 100 mM. The solution may further comprise a labeled ligand and/or a target compound.

In a second embodiment for functional assays according to a GTP-analogue-binding profile approach, the buffered solution is similar to the binding solution, but further includes a GTP-analogue, a GDP salt, and an anti-oxidant reagent. The solution has a composition comprising: a) a buffer reagent with a pH in the range of about 6.5 to about 7.9; b) a divalent inorganic salt, optionally together with a monovalent inorganic salt, at a concentration from about 1 mM to about 500 mM; c) GDP salt at a concentration of about 0.5 mM to about 50 mM (preferably 1-10 mM); and optionally a combination of d) a blocker reagent at a concentration of about 0.01 wt. % to about 2 wt. % of the composition, e) protease-inhibitor at a concentration of about 0.001 mM to about 100 mM, or f) an anti-oxidant reagent at a concentration of 0.01 mM to about 100 mM.

According to another aspect of the present invention, a method for reducing background signal due to non-specific binding of either a labeled-ligand or GTP-analogue to a substrate surface is described. In one embodiment the method comprises: a) providing a buffered solution containing a blocker reagent; b) applying the solution to an array of GPCRs; c) applying a second solution containing a labeled ligand or GTP-analogue, in either the absence or presence of a target compound; and d) monitoring or determining the binding of the labeled ligand to a receptor, or the GTP-analogue to a G-protein coupled with the receptor in the array. The method may further involve a washing and dry step before data acquisition. Alternatively, the method may comprise: a) providing a solution containing a blocker reagent and a labeled ligand or GTP-analogue, in either the absence or presence of a target compound; b) applying the solution to a microarray of GPCRs; and c) monitoring or determining the binding of the labeled ligand to a receptor, or the GTP-analogue to a G-protein coupled with the receptor in the microarray.

Additional features and advantages of the present invention will be revealed in the following detailed description. Both the foregoing summary and the following detailed description and examples are merely representative of the invention, and are intended to provide an overview for understanding the invention as claimed.

BRIEF DESCRIPTION OF THE FIGURES

FIGS. 1A & 1B are false color fluorescent images of arrays having two replicate microspots of neurotensin receptor Subtype-1 (NTR1), after binding with 2 nM Bodipy-TMR-neurotensin 2-13 in a binding buffer, respectively, in the presence or absence of 100 mM NaCl.

FIG. 1C is a graph summarizing the effect of the presence or absence of NaCl on the total binding signal of NTR1 microarrays in FIGS. 1A and 1B.

FIGS. 3A & 3B are false-color images of an array having in four columns: NTR1, µ-opioid receptor, motilin receptor (MR1), and CHO control membranes (left to right). The images are taken after the array is incubated with a functional assay buffer solution containing 2 nM of $^{35}$S-GTPγS, in the presence (FIG. 3A) and absence (FIG. 3B) of 100 nM dynorphin A and 100 nM nurotensin. Dynorphin A is an agonist to mu opioid receptor; neurotensin is an agonist to neurotensin receptor subtype 1 (NTR1) receptor.

FIGS. 3C & 3D, respectively, are graphs of the total counts of receptor microspots in FIGS. 3A and 3B, indicating the respective activated and basal counts, respectively, of total detected signal in the presence and absence of the agonist.

DETAILED DESCRIPTION OF THE INVENTION

Section I

Definitions

Figure 2A:
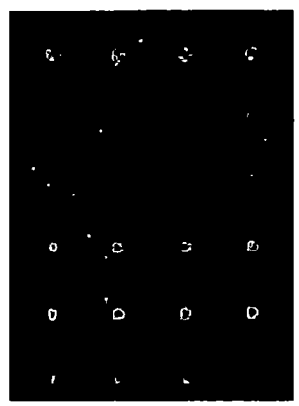
FIGS. 2A & 2B are false-color images in terms of Cy3/Cy5 ratio of two microarrays, each having six different GPCR-membrane preparations. The images are taken after a buffered solution for binding assays was reacted with the arrays.

Before describing the present invention in detail, this invention is not necessarily limited to specific compositions, reagents, process steps, or equipment, as such may vary. As used in this specification and the appended claims, the singular forms "a," "an," and "the" include plural referents unless the context clearly dictates otherwise. It is also to be understood that the terminology used herein is for the purpose of describing particular embodiments only, and is not intended to be limiting. All technical and scientific terms used herein have the usual meaning conventionally understood by persons skilled in the art to which this invention pertains, unless context defines otherwise.

The term "ligand" refers to a chemical molecule or biological molecule that can bind readily to a receptor with a specific binding affinity constant.

The term "labeled-ligand" refers to either a fluorescently labeled or radioactive isotope-labeled or hapten-labeled (e.g., biotin) or gold-nano-particle labeled ligand.

The term "cocktail" refers to a medium (e.g., buffered or aqueous solution) having a mixture either of different labeled ligands or of different compounds. Alternatively, in some embodiments, a mixture of both ligands and compounds may be present together in solution.

The term "compound," "target," or "target compound" as used herein refers to a biological molecule, biochemical or chemical entity, molecule, or pharmaceutical drug candidate to be detected.

The term "biological molecule" or "biomolecule" refers to any kind of biological entity, including, such as, modified and unmodified nucleotides, nucleosides, peptides, polypeptides, proteins, lipids, or saccharides.

The term "cognate," "corresponding," or "paired" refers to the reciprocal moiety of a molecule to another; in particular, a ligand that can bind specifically to a given receptor is called a ligand-receptor pair.

The term "biospot" or "microspot" refers to a discrete or defined area, locus, or spot on the surface of a substrate, containing a biological or chemical probe.

The term "GPCR" refers to a guanine nucleotide-binding protein-coupled receptor. The GPCR can have either a natural or modified sequence.

The term "GPCR membrane" or "GPCR membrane fragment" refers to a biological membrane or cell membrane fragment having a GPCR embedded within a membrane layer, or a micelle having a GPCR reconstituted within the micelle.

The term "GPCR microspot" refers to a microspot containing a deposit of G-protein coupled receptors (GPCRs). The corresponding microspots are referred to as "probe microspots," and these microspots are arranged in a spatially addressable manner to form a microarray.

The term "GTP-analogue" refers to a GTP molecule that is modified with a label moiety, either for example fluorescent dye, radioactive isotope, or Eu-chelates.

The term "probe" or "receptor probe" refers to a receptor molecule (e.g., GPCR), which according to the nomenclature recommended by B. Phimister (*Nature Genetics* 1999, 21 supplement, pp. 1-60.), is immobilized to a substrate surface. Preferably, probes are arranged in a spatially addressable manner to form an array of microspots. When the array is exposed to a sample of interest, molecules in the sample selectively and specifically binds to their binding partners (i.e., probes). The binding of a "target" to the probes occurs to an extent determined by the concentration of that "target" molecule and its affinity for a particular probe.

The term "substrate" or "substrate surface" as used herein refers to a solid or semi-solid, or porous material (e.g., micro- or nano-scale pores), which can form a stable support. The substrate surface can be selected from a variety of materials.

The term "functionalization" as used herein relates to modification of a solid substrate to provide a plurality of functional groups on the substrate surface. The phrase "functionalized surface" as used herein refers to a substrate surface that has been modified to have a plurality of functional groups present thereon. The surface may have an amine-presenting functionality (e.g., γ-amino-propylsilane (GAPS) coating), or may be coated with amine presenting polymers such as chitosan and poly(ethyleneimine).

Section II

Description

Previously, we demonstrated that one may fabricate GPCR microarrays using conventional robotic pin printing technologies and cell membrane preparations containing GPCRs from a cell line over-expressing the receptor. (U.S. patent application Ser. Nos. 09/974,415 (U.S. Patent Publication No. 2002/0019015 A1), and 09/854,786, (U.S. Patent Publication No. 2002/0094544 A1) the contents of which are incorporated herein by reference). Also, we have described certain methods for fabricating biological membrane microarrays on substrates presenting certain surface chemistries. (U.S. patent application Ser. No. 10/300,954, incorporated herein by reference.) These kinds of arrays can be prepared under ambient conditions, stored at about 4° C., and still retain their functionality for an extended period of time thereafter. In addition, we have described the use of GPCR micrarrays for compound-profiling and screening applications using multiplexed binding and functional assays. (See, U.S. patent application Ser. No. 10/639,718, the content of which is incorporated herein by reference.)

The interaction of GPCRs with ligands, or target compounds, is relatively complicated. This fact is due in part to the diversity of compounds and ligands, and the number of different functional roles (i.e., agonist, partial agonist, inverse agonist, antagonist) that different target compounds may play when acting on a single receptor. During the development of a superior assay technology, several parameters should be kept in mind. For instance, to achieve physiologically and pharmacologically relevant binding profiles of target compounds and labeled ligands to the receptor, a buffer composition should be optimized according to the specific nature of receptor probe species in the array and/or characteristics of target compounds. Also, a buffer composition should maintain reasonable mechanical stability of receptor microspots, in which the receptor membranes are generally immobilized non-covalently on a substrate. Moreover, since different types of assay format each may require the inclusion of a different combination or varied set of reagents, a single, basic, universal buffer composition for both binding and functional assay is difficult to achieve.

Having these parameters in mind, the present invention provides buffered solution compositions for two major classes of assays that employ GPCR microarrays. These assay formats are multiplexed binding assays and functional assays. For binding assays, the present buffered solution has a composition that not only maximizes the efficiency and specificity of binding reaction of labeled ligands or target compounds with the receptors in the arrays, but also can result in physiologically and pharmacologically relevant binding profiles with improved signal to background ratio. The buffered solution and associated methods of use can reduce the overall background signal that is mainly due to non-specific binding of labeled ligands to an array substrate surface.

One the other hand, for functional assays which are based on monitoring the activation of G protein coupled with the receptor, the present buffered solution not only provides optimal binding of target compounds to the receptors in the array, but also maximizes an increased percentage of GTP-analogue binding to heterotrimeric G-proteins coupled with receptors in the presence of an agonist compound. The increased binding of GTP-analogue is due to the stimulation or promotion of GTP analogue to the G proteins by agonist-induced receptor activation and sequential G-protein activation. At the same time, the present invention and method of use could give rise to reduced background signal and improved assay sensitivity.

Furthermore, to achieve superior assay performance using GPCR arrays and to reduce non-specific binding of labeled ligands or GTP-analogues to a background surface, we propose a method which incorporates a blocker reagent in the assay buffer solution composition.

A. Binding Assay Solution

As touched upon in the foregoing, the interaction of GPCRs with ligands and target compounds is rather complicated; interactions depend mostly on the specific nature of receptors, the ligands and target compounds, as well as the buffer compositions.

Although GPCRs are generally widely distributed in numerous tissues, some GPCRs are preferably and highly distributed in certain types of tissues. For example, some receptors, including the muscarinic acetylcholine receptor, dopamine 2 receptor, histamine 2 receptor, serotonin 4 receptor, and prostaglandin receptor, are prominently distributed in the gastrointestinal system. Some other receptors, including serotonin 1A/1D and 2A/2C receptor, neurotensin 1 and 2 receptors, opioid receptors (mu, delta, kappa, ORL-1), and dopamine 2/3 receptors, are prominently distributed in the central nervous system (Stadel, J. M., et al. *TIPS* 1997, v. 18, 430-437). The nature and compositions of bio-fluids could differ significantly from one tissue system to another. Therefore, it follows that the physiological binding conditions for nature ligands to their paired receptors could also differ significantly.

On the other hand, although GPCRs share some characteristic motifs, GPCRs differs in sequences and structure. For example, in the trans-membrane (TM) II an Asp residue is conserved in most GPCRs (e.g., neurotensin receptor subtype 1; NTR1), but not certain other GPCRs (e.g., neurotensin receptor subtype 2; NTR2). Natural agonists bind to receptors with the TM II Asp residue more sensitively to sodium ions in an assay buffer than those do to receptors absent the TM II Asp residue. (Martin, S. et al., "Pivotal Role of an Aspartate Residue in Sodium Sensitivity and Coupling to G-Proteins of Neurotensin Receptors," *Molecular Pharmacology*, 1999, 55, 210-215). The presence of sodium ions, at a concentration as low as about 20 mM, inhibits the binding of radio-labeled neurotensin to NTR1 by at least 50% ($IC_{50}$ of 18 mM). In contrast, one observes a very weak effect of sodium ions on the binding of radio-labeled neurotensin to mouse NTR2 ($IC_{50}$ of 225 mM). Other receptors also show similar allosteric modulation of ligand-receptor binding by monovalent cations include $\alpha_{2A}$ and $\alpha_{2B}$ adrenergic receptors, μ opioid receptor, $D_2$ dopamine receptor, SST2 somatostatin receptor, $\beta_2$ adrenergic receptor, and adenosine receptors (Ceresa, B. P., & Limbird, L. E., "Mutation of an Aspartate Residue Highly Conserved Among G-Protein-Coupled Receptors Results in Non-Reciprocal Disruption of $\alpha_2$-Adrenergic Receptor-G-Protein Interactions," *J. Biol. Chem.*, 1994, 269, 29577-29564). Monovalent cations ($Na^+ \geq Li^+ >> K^+$) have reciprocal effects on agonist versus antagonists interactions at the receptor.

The effect of NaCl on the binding of natural agonists to receptors in a microarray also has been observed as presented in FIG. 1. False color images in FIGS. 1A and 1B show the binding of labeled-agonist to NTR1 receptors. The graph of FIG. 1C signifies that NaCl strongly influences the binding of BT-NT to NTR1.

Ligands for GPCRs are very diverse, including biogenic amines, peptides and proteins, lipids, nucleotides, excitatory amino acids and ions, small chemical compounds, etc. (Morris, A. J., and Malbon, C. C., "Physiological Regulation of G-Protein-linked Signaling," *Physiol. Rev.*, 1999, 79, 1373-1430.) Generally, a particular GPCR could couple to one or more trimeric G proteins in a particular cell line. The binding affinities of agonists to a GPCR depend on the coupling state of the receptor with its G proteins. Compounds that bind with a receptor might have different functionalities, such as agonism, antagonism, super-agonism or inverse agonism. The binding sites involved might be different for different compounds binding to the same receptor.

In sum, buffer compositions for binding assays could not only affect the interaction of receptors with ligands or target compounds, but also the functionality of the membrane proteins. For example, some GPCR-ligand interactions depend strongly on the presence of particular divalent cations such as $Mg^{2+}$ or $Mn^{2+}$. In addition, the buffer composition also may have a negative impact on the physical stability and packing of receptor-containing lipid membranes that are immobilized on the substrate surfaces non-covalently, therefore decreasing array performance and assay robustness.

In solving the issues associated with achieving physiologically and pharmacologically relevant binding profiles for target compounds and labeled ligands to the receptor, an ideal buffer composition should meet at least following criteria: (1) the binding profiling (affinity, specificity, selectivity) of labeled ligands and target compounds to their paired receptors should be physiologically and pharmacologically relevant; (2) the microarrays should be stable through the bioassays under assay buffer conditions; (3) the background signals should be minimal.

According to the present invention, a buffered solution has a composition comprising: a) a buffer reagent with a pH in the range of about 6.5 to about 7.9; b) an inorganic salt of either a monovalent or divalent species, at a concentration from about 1 mM to about 500 mM; and optionally a combination of c) a blocker reagent at a concentration of about 0.01 wt. % to about 2 wt. % of the composition, or d) protease-inhibitor at a concentration of about 0.001 mM to about 100 mM.

Preferably, the pH value is in a range of about 6.8-7.8, and more preferably about 7.4-7.5. The pH buffer is made from a solution having commonly used pH control reagents selected from Tris-HCl, HEPES-KOH, TES-NH$_4$OH, MOPS, acetate, citrate, citrate-phosphate, sodium-phosphate, maleate, or succinate buffers. Preferably, the reagents are Tris-HCl, HEPES-KOH, MOPS, or sodium-phosphate. The pH buffer reagent is preferably at a concentration of about 1-200 mM, or more preferably about 10-50 mM.

The inorganic salt may be either a monovalent or a divalent species, or a combination of the two, each at a concentration of about 1-100 mM, preferably about 1-50 mM. The inorganic salt may be selected from NaCl, KCl, CaCl$_2$, MgCl$_2$, MgSO$_4$, or MnCl$_2$.

The composition may further include a labeled ligand and/or a target compound.

Generally, the blocker reagent is characterized as a reagent that reduces background signal and does not interfere with the binding of a target molecule with the probe receptors within a biological membrane microspot. The blocker reagent can be either a hydrophilic polymer, a biopolymer, or a water-soluble protein. A hydrophilic polymer can be: dextran, polyvinyl alcohol, poly(ethylene glycol), poly(anetholsulfonate), poly(vinyl sulfate), CM-Dextran, dextran sulfate, beta-cyclodextrin, poly(acrylic acid), poly(sodium 4-styrene sulfonate). A biopolymer can be a poly-glutamate acid, or DNA, and a water-soluble protein can be albumin (e.g., bovine serum albumin (BSA)), casein, dry milk, or wheat germ agglutinin. The preferred blocker reagent is a water soluble protein.

The buffered assay solution preferably is protease-free. Protease inhibitors, however, can be included. Examples of protease inhibitors may include ethylene diamine-tetra-acetic acid (EDTA), ethylene bis-(oxyethylenenitrilo)-tetra-acetic acid (EGTA), phenyl methyl sulforyl fluoride (PMSF), bacitracin, 4-(2-aminoethyl)benzenesulfonyl fluoride (AEBSF), aprotinin, 1,10-phenanthroline, E-64, antipain, aprotinin, benzamidine HCl, bestatin, chymostatin, $\epsilon$-aminocaproic acid, N-ethylmaleimid, leupeptin, pepstatin A, phosphoramidon, trypsin inhibitor, and any combination of these. Preferably, EDTA or EGTA is always included in the composition of the buffered assay solution to reduce damage from free-radicals and protease-induced degradation of receptors.

Figure 2C:
FIGS. 2C & 2D, respectively, are graphs of the percent of total detected signal in the presence and absence of 1 µM telenzepine.
Figure 2B:
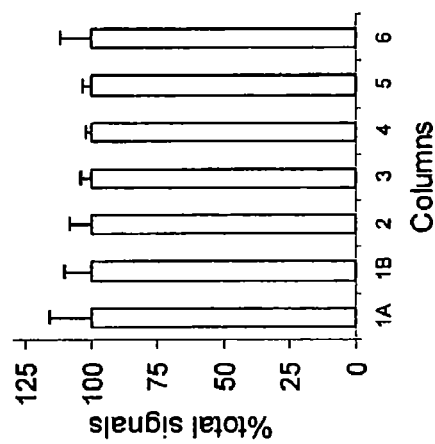
Figure 2D:
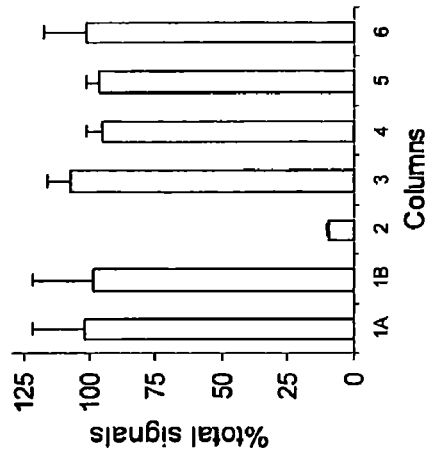

A single buffered binding solution composition, according to the invention—including for example, 50 mM Tris-HCl, pH 7.4, 10 mM MgCl$_2$, 1 mM EDTA, 0.1 wt. % BSA—is used for multiplexed competitive binding assay. The results are presented in FIG. 2. FIGS. 2A and 2B show false-color fluorescence images in Cy3/Cy5 ratio of two membrane microarrays of six different GPCR-membrane preparations (from left to right: HEK cell membrane as control, muscarinic receptor subtype 1 (M1), motilin receptor (MOTR), neurotensin receptor subtype 1 (NTR1), opioid receptor like subtype 1 (ORL1) and delta 2 opioid receptor (OP1)). Each microarray is incubated with a buffered solution containing a mixture or cocktail of labeled-ligands in the presence or absence of 1000 nM of motilin. The labeled-ligands are 2 nM Cy3B-telenezepine (from Amersham), 4 nM BT-motilin 1-16, 4 nM Cy5-neurotensin 2-13, 2 nM Cy5-nociceptin 1-13, and 4 nM Cy5-naltrexone. Graphs of FIGS. 2C and 2D signify the specific and selective inhibition of the binding of labeled ligands to M1 receptors by unlabeled telenzepine, as evidenced in the relative total signal percentage in the presence (C) and absence (D) of 1 uM telenzepine in column 2. Telenzepine is an antagonist for M1 receptor alone. Samples 1A and 1B, in the graphs, show the HEK control signals in Cy3 and Cy5, respectively.

B. Functional Assay Solution

Functional assays afford several advantages over binding assays. For instance, functional assay use a single labeled biological molecule, e.g., GTP-analogue, to study, screen or profile target compounds, instead of a mixed solution of labeled-ligands for multiplexed binding assays. Further, functional assays can provide more information (i.e., biological functionality beyond mere binding profiles) about the interaction of a target compound with its receptor(s).

Upon agonist binding to a receptor, the GPCR undergoes conformational changes that prompt GTP binding to receptor-coupled $G_\alpha$, protein. This property gives rise to one of the most useful measures of GPCR activation of G protein. To date, a couple of analogues have been used for both heterogeneous- and homogeneous-format functional assays. These analogues include radioactive $^{35}$S-GTP$\gamma$S and Eu-GTP.

For functional assay applications that employ a GTP-analogue binding format, the present invention offers a buffered assay solution that can improve assay performance and sensitivity. The composition of the functional assay solution is similar to that of the binding assay solution, but not identical because a functional assay should not only offer physiological relevant binding profiles of target compounds, but also should maximize the activation signals, which is manifested as a binding of the GTP-analogue with the G-proteins coupled with receptors.

The buffered assay solution has a composition comprising: a) a buffer reagent with a pH in the range of about 6.5 to about 7.9; b) a divalent inorganic salt, optionally together with a monovalent inorganic salt, at a concentration from about 1 mM to about 500 mM; c) guanosine 5'-diphosphate (GDP) salt at a concentration of about 0.5 mM to about 50 mM (1-10 mM); and optionally a combination of: d) a blocker reagent at a concentration of about 0.01 or 0.1 wt. % to about 2 wt. % of the composition, e) protease-inhibitor at a concentration of about 0.001 mM to about 100 mM, or f) an anti-oxidant reagent at a concentration of 0.01 mM to about 100 mM. Although most components and the pH values of the functional assay solution are similar, the major distinctions between the binding assay and functional assay solutions involve the inclusion of a GTP-analogue, a GDP salt, an anti-oxidant reagent, and varied inorganic salt species.

Figure 4:
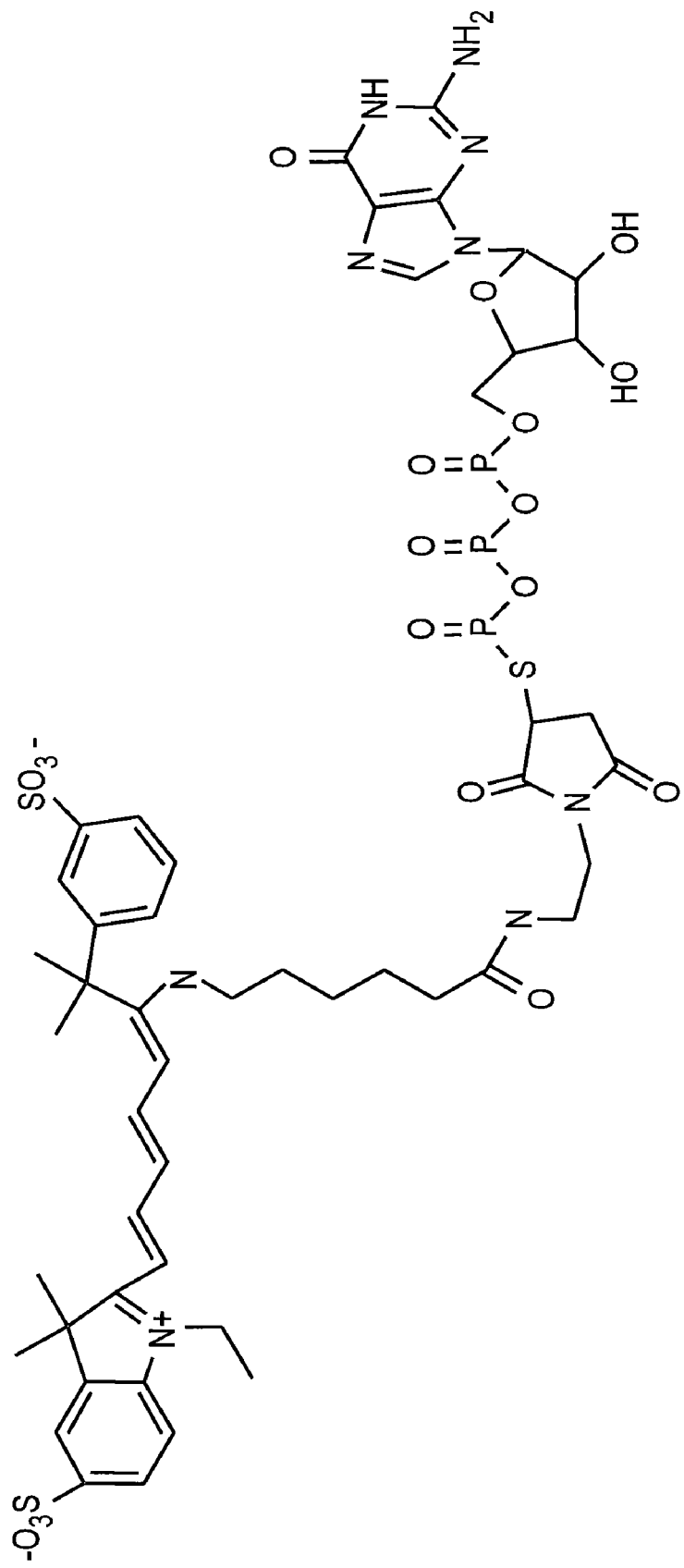
FIG. 4 represents the chemical structure of Cy5-GTPγS, as synthesized for the invention.

The GTP-analogue may include: fluorescein-GTP$\gamma$S, Bodipy-fluorescein-GTP$\gamma$S, Bodipy-TMR-GTP$\gamma$S, Cy3-GTP$\gamma$S, Cy5-GTP$\gamma$S, Eu-GTP, $^{35}$S-GTP$\gamma$S. FIG. 3 presents the structure of Cy5-GTP$\gamma$S, as synthesized according to the invention. In the synthesis, for example, a GTP$\gamma$S tetralithium salt (Calbiochem) is dissolved in about 20 mM sodium bicarbonate at a pH ~9 to a concentration of about 15 mM. A Cy5 maleimide monoreactive dye (Amersham) is dissolved in DMF to a concentration of about 15 mM. Both solutions are flushed with nitrogen, and mixed together. After a certain amount of time (e.g., 0.5 to 24 hrs), the resulting solution is loaded into a reverse phase high-performance-liquid-chromatography (HPLC). One major product is collected and examined by UV spectrometry, mass-spectrometry, and NMR, which confirmed the structure as shown in FIG. 4.

The GDP salt may be selected from a group consisting of: lithium-, sodium-, and Tris-GDP salts. The anti-oxidant reagent may include sodium ascorbate, ascorbic acid, carotenoid lycopene, α-tocopherol, β-carotene, sodium azide, at a concentration in a range of about 0.001 wt. % to about 0.5 wt. %.

FIG. 3 illustrates agonist-prompted binding of $^{35}$S-GTPγS to GPCR microarrays using a buffered solution according to the present invention. Microarrays are incubated with at in a functional buffer containing 2 nM $^{35}$S-GTPγS in the absence and presence of a cocktail agonists (100 nM neurotensin and 100 nM dynorphin A). The buffered solution comprises 75 mM Tris-HCl, pH 7.4, 1 mM EDTA, 100 mM NaCl, 10 mM $MgCl_2$, and 3 μM GDP. Under the optimized buffer conditions, both the activation of agonist-induced receptors (NTR1 and mu, but not CHO control and MOTR in the same arrays) and the sequential activation of G proteins coupled with the receptors can be observed simultaneously, as evidenced by the increased signals due to the binding of $^{35}$S-GTPγS.

Figure 5:
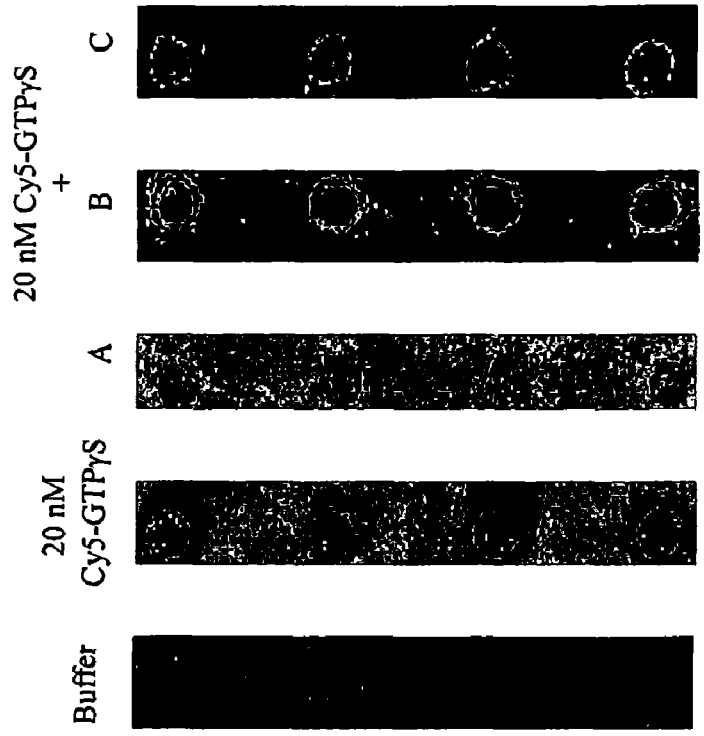
FIG. 5 are fluorescence images of β1-adrengeric receptor arrays on a GAPS-coated surface after binding with Cy5-GTPγS in the absence or presence of three different blocking reagents: (A) 0.5% BSA; (B) 0.1% poly-glutamate; (C) 0.5% poly-anetholsulfate. The concentration of Cy5-GTPγS is 20 nM.

An example of the effect of blocker reagents on binding of labeled-ligands or GTP-analogues is shown in FIG. 5. Blocker reagents in columns A-C are: A=0.5% BSA; B=0.1% poly-glutamate; C=0.5% poly-anetholsulfate. Data, derived from fluorescence images of β1 arrays after bioassays in Cy5 channel, suggest that: (1) there is a negligible auto-fluorescence of membrane microspots; (2) high fluorescence background of membrane arrays is present after the binding of Cy5-GTPγS in the absence of a blocking reagent—partially due to the non-specific binding of the probe to GAPS; and (3) presence of BSA in binding solution reduces the fluorescence background by about 50%, while the presence of the other two blockers can greatly reduces the fluorescence background from non-specific binding by about 70-90%, without detrimentally effecting the total signal of fluorescence of the membrane microspots.

C. Methods

Fluorescence-based detection schemes for microarrays have certain advantages and disadvantages. An advantage is that a fluorescence technology is highly sensitive relative to other methods. A disadvantage is that proteins, especially biological membrane preparations; have relatively high intrinsic auto-fluorescence, particularly in low (~400-590 nm) wavelength channels (e.g., FITC and Cy-3). An approach to overcome this problem is to use a fluorescence dye having a longer wavelength emission, such as Cy-5. Use of a probe labeled with a dye of long wavelength emission would allow one to avoid the auto-fluorescence of membranes in the microspots as well as the surface.

The non-specific binding of labeled targets to background, however, raises significant concerns for microarray technologies. For example, we have observed high fluorescence background when Bodipy-FL-GTPγS is used as a probe for GPCR functional assays. The background is mainly due to the non-specific binding of highly negatively charged Bodipy-FL-GTPγS to the positively charged GAPS surface. Reagents that can significantly reduce the background due to the non-specific binding of the probe to the surface would be extremely helpful.

Hence, another approach to improve assay performance by means of reducing background involves using blocker reagents. According to the present invention, we provide a method of reducing background signal due to non-specific binding of a labeled-ligand or GTP-analogue to a substrate surface. The method comprises: a) providing a buffered solution containing a blocker reagent; b) applying said solution to an array of GPCRs; c) applying a second solution containing a labeled ligand or GTP-analogue, in either the absence or presence of a target compound; and d) monitoring or determining the binding of said labeled ligand to a receptor, or said GTP-analogue to a G-protein coupled with said receptor in said array. The method may further comprise a washing and dry step before data acquisition. In an alternative simplified embodiment, one may providing a solution containing a blocker reagent and a labeled ligand or GTP-analogue, in either the absence or presence of a target compound; applying said solution to a microarray of GPCRs; and monitoring or determining the binding.

D. Empirical Examples

1. Membrane Preparations

After obtaining commercial membrane fractions containing human neurotensin receptor subtype 1 (NTR1), 11 adrenergic receptor, opioid-like receptor subtype 1 (ORL1), motilin receptor (MOTR) CHO cell membranes, HEK cell membranes (Perkin Elmer Life Sciences (Boston, Mass.)), and delta-2 opioid receptor (OP1) (Euroscreen (Gosselies, Belgium)), these membrane suspensions were either directly used or reformulated in buffer according to the formulation in co-assigned U.S. patent application Ser. No. 10/651,554.

2. Synthesis and Characterization of Fluorescently Labeled Ligands

Neurotensin (2-13), nociceptin (1-13), naltrexone and motilin (1-16) were obtained commercially from Sigma (St. Louis, Mo.), while solutions of the peptides in bicarbonate or phosphate buffer were treated with solutions of N-hydroxysuccinimidyl (NHS) derivatives of the fluorescent dyes in DMSO to synthesize Cy5-nociceptin (1-13), Bodipy-TMR-motilin (1-16) and Cy5-neurotensin (2-13). Cy5-naltrexone is synthesized following the method developed by Luke et al. (Luke, M. C., Hahn, E. F., Price, M. & Pasternak, G. W. Irreversible opioid agonists and antagoinsts: V. hydrazone and acylhydrazone derivatives of naltrexone. Life Sciences 1998, 43, 1249-1256). The labeled compounds are purified by means of reverse phase HPLC (Alliance System 2690 and Nova-Pak $C_{18}$ column, Waters Inc, Milford, Mass.), characterized by mass spectroscopy (IonSpec HiRes MALDI FT-mass spectrometer, IonSpec, Lake Forest, Calif.), and tested for specificity using GPCR microarrays (s) and ligand-binding assays on filter plates. MALDI-MS (m/z) (M+H): 2201 for Cy5-NT (2-13), 994 for Cy5-naltrexone, 2480 for Bodipy-TMR-motilin (1-16), and 2020 for Cy5-nociceptin (1-13).

3. Microarray Fabrication

Using a quill-pin printer (Cartesian Technologies, Model PS 5000) equipped with software for programmable aspiration and dispensing, one can fabricate GPCR microarrays. For printing, 5-7 μl of each GPCR suspension is added to different wells of a 384 well microplate. Replicate microspots were obtained using a single insertion of the pin into the solution. To prevent contamination due to carry-over between different GPCR suspensions, an automatic wash and dry cycle was incorporated. After printing, the arrays were incubated in a humid chamber at room temperature for one hour, and then used for ligand binding experiments.

4. Binding Assays

For the binding assays, each individual array was incubated with 10 µl of a solution containing labeled ligand(s) at a particular concentration in the absence and presence of varying amounts (0-1000 nM) of unlabeled compounds. The binding buffer used for all experiments was Tris-HCl (50 mM, pH 7.4) containing 10 mM $MgCl_2$, 0.1% BSA and 1 mM EDTA.

5. Functional Assays

For the functional assays, each individual array was incubated with 15 µl of a solution containing $^{35}$S-GTPγS at a particular concentration in the absence and presence of 100 nM neurotensin and 100 nM dynorphin A. The functional assay buffer used for all experiments was 75 mM Tris-HCl, 7.4 containing 10 mM $MgCl_2$, 100 mM NaCl, 0.1% BSA, 3 µM GDP, and 1 mM EDTA.

6. Fluorescence Measurements

After executing the binding assays, the microarrays are washed and dried, and then examined using Genepix scanner 4000 (Axon Instruments, Union City, Calif.). Using Genepix software, resulting data is analyzed. Each data point in the plots represents the average of at least three replicate micospots. Using non-linear regression analysis (Graphpad PRISM, Graphpad Software Inc., San Diego, Calif.), one can estimate $K_d$ and $IC_{50}$.

7. Radioactivity Measurements

After executing functional assays, the microarrays are washed and dried, and then exposed overnight to a screen specific for $^{35}$S isotope. Afterwards, the screen is imaged using Typhoon 9400 (Amersham Biosciences). Data analysis is carried out using Genepix software, wherein each data point in the plots represents the average of at least three replicate micospots.

The present invention has been described both in general and in detail by way of examples. Persons skilled in the art will understand that the invention is not limited necessarily to the specific embodiments disclosed. Modifications and variations may be made without departing from the scope of the invention as defined by the following claims or their equivalents, including equivalent components presently known, or to be developed, which may be used within the scope of the present invention. Hence, unless changes otherwise depart from the scope of the invention, the changes should be construed as being included herein.

We claim:

1. A method of reducing background signal due to non-specific binding of a labeled-ligand or GTP-analogue to a substrate surface, the method comprising:
   providing a buffered solution containing a blocker reagent;
   applying said solution to an array of GPCRs, G-protein coupled receptors;
   applying a second solution containing a labeled ligand or GTP-analogue, in either the absence or presence of a target compound; and
   monitoring or determining the binding of labeled ligand to a receptor, or the GTP-analogue to a G-protein coupled with the receptor in the array.

2. The method according to claim 1, wherein the method further comprises a washing and drying step before data acquisition.

3. A method of reducing background signal due to non-specific binding of a labeled-ligand or GTP-analogue to a substrate surface, the method comprising:
   providing a solution containing a blocker reagent and a labeled ligand or GTP-analogue, in either the absence or presence of a target compound;
   applying the solution to a microarray of GPCRs, G-protein coupled receptors; and
   monitoring or determining the binding of the labeled ligand to a receptor, or the GTP-analogue to a G-protein coupled with the receptor in the microarray.

* * * * *